United States Patent [19]

Berthiaume

[11] Patent Number: 5,161,534
[45] Date of Patent: Nov. 10, 1992

[54] TOOL FOR MANIPULATING A MEDICAL GUIDEWIRE

[75] Inventor: William A. Berthiaume, Hudson, Mass.

[73] Assignee: C. R. Bard, Inc., Murray Hill, N.J.

[21] Appl. No.: 755,094

[22] Filed: Sep. 5, 1991

[51] Int. Cl.⁵ .............................................. A61B 6/00
[52] U.S. Cl. .................................. 128/657; 604/159; 226/127
[58] Field of Search ............... 128/657, 772; 606/180, 606/225; 604/95, 117, 159, 280; 24/136 L, 136 R; 226/127, 196

[56] References Cited

U.S. PATENT DOCUMENTS

| | | | |
|---|---|---|---|
| 4,380,433 | 4/1983 | Ellman et al. | 226/127 |
| 4,509,233 | 4/1985 | Shaw | 24/136 R |
| 4,726,369 | 2/1988 | Mar | 128/657 |
| 4,829,999 | 5/1989 | Auth | 128/303 R |
| 4,858,810 | 8/1989 | Intlekofer et al. | 604/159 |

OTHER PUBLICATIONS

USCI Drawing No. SP4601418 dated Sep. 28, 1989 entitled "Product: Steering Handle Assembly".

Primary Examiner—Max Hindenburg
Attorney, Agent, or Firm—Wolf, Greenfield & Sacks

[57] ABSTRACT

A laterally attachable and detachable tool for manipulating a guidewire includes a cylindrical body that terminates in a collet. A nut is threaded to the collet and can be tightened to draw the collet arms inwardly. The body and the nut each include a lateral slot of a width to receive the guidewire. The slot in the nut is registrable with the slot in the body to form a continuous slot, receptive to the guidewire, along the length of the tool.

11 Claims, 1 Drawing Sheet

TOOL FOR MANIPULATING A MEDICAL GUIDEWIRE

FIELD OF INVENTION

The present invention relates to a tool for manipulating a medical guidewire and, more particularly, to a tool that is longitudinally and laterally attachable to and detachable from the guidewire.

BACKGROUND OF THE INVENTION

Guidewires are well known for placing and guiding catheters and other devices in the vascular network of the human body. In a common type of procedure a guidewire is inserted percutaneously into an easily accessed blood vessel. The guidewire then is manipulated to steer the guidewire through the vascular network until the distal end (the end inside the patient) reaches a desired location. The catheter may be inserted preassembled with the guidewire or the catheter may be inserted and advanced over a previously placed guidewire.

The steerability of the guidewire is important especially when a tortuous path must be navigated to reach the target site as is commonly encountered when placing a catheter in the coronary arteries. Steering is executed from the proximal end of the guidewire (outside of the patient) by rotating, pushing and pulling on the guidewire to cause corresponding movement at the distal tip of the wire. The distal tip typically has a slight bend so that when rotated it can be directed toward a selected one of several vascular branches. The distal tip of the guidewire typically is radiopaque so that its movement can be observed under x-ray fluoroscopy. Steering of the guidewire directly by hand has proven difficult because of the small diameter (0.010" to 0.038") and high flexibility of the guidewire. In addition some guidewires have a lubricious surface coating and tend to slip out of the user's grasp.

Steering tools have been developed to alleviate the foregoing problems. Typical is a device sold under the trade designation Steering Handle by U.S.C.I., a division of C.R. Bard, Inc. The device includes a hollow cylindrical body having a central bore and tapered collet for firm attachment to the guidewire. The device is substantially greater in diameter than the guidewire and is more easily gripped and rotated. The device is threaded onto the guidewire over an end of the guidewire and is slid along the guidewire to a location convenient for the physicians. The collet then is tightened securely around the guidewire.

To avoid having to slide the steering tool along the guidewire, laterally mountable steering devices have been developed. U.S. Pat. No. 4,726,369 discloses a steering tool including a resilient cylindrical body with an axial bore and a surrounding sleeve. Radial, longitudinally extending slots on the sleeve and the cylindrical body are aligned to form a continuous slot through which the guidewire can be laterally inserted and removed. To hold the guidewire in place, the sleeve is squeezed causing the resilient cylindrical body walls to compress against the guidewire. The device disclosed in U.S. Pat. No. 4,726,329 is not well suited for use when the traditional longitudinal mounting procedure is required or preferred.

SUMMARY OF THE INVENTION

The present invention is a tool for manipulating a guidewire. The tool either may be laterally or longitudinally mounted to the guidewire. The tool comprises an elongated main body that includes a cylindrical portion and a collet portion. A bore extends axially through the main body and opens laterally through the surface thereof. The collet portion includes four circumferentially spaced fingers which respectively are separated by slots extending radially through the surface of the collet. The surface of the collet portion is threaded for engagement with a nut. The nut includes a laterally extending slot that is alignable with the lateral opening in the elongated main body. The lateral opening in the elongated main body and the laterally extending slot in the nut are sized to receive the guidewire. When aligned, the laterally extending slot in the nut and the lateral opening in the elongated main body form a continuous elongated lateral slot that permits side-mounting of the tool onto the guidewire. After the tool is mounted about the guidewire, the nut is tightened until the guidewire is securely engaged between the inwardly compressed collet arms.

It is among the general objects of the invention to provide a tool that is mountable to a guidewire that already is positioned within the patient's body.

It is a further object of the invention to provide a tool that is mountable either laterally or longitudinally to a guidewire.

DESCRIPTION OF THE DRAWINGS

The foregoing and other objects and advantages of the invention will be appreciated more fully from the following drawings in which.

DESCRIPTION OF THE PREFERRED EMBODIMENTS

Figure 1:
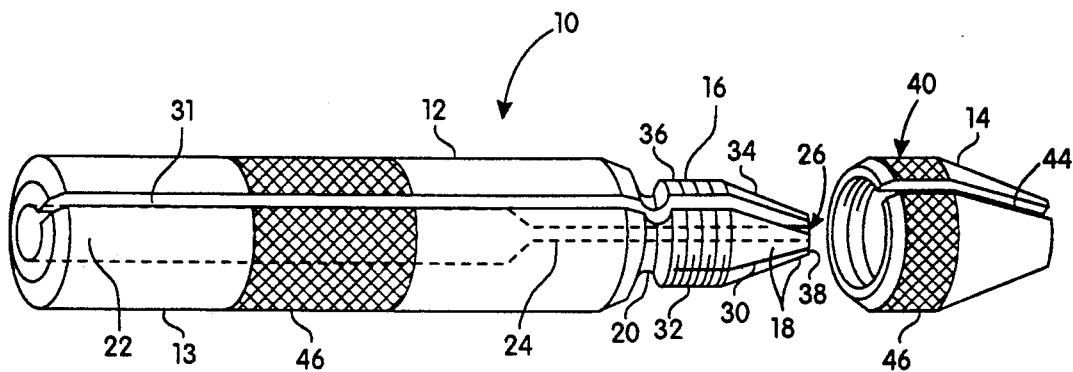
FIG. 1 is a perspective view, partly in phantom, of the guidewire manipulating tool in accordance with the invention.

The guidewire manipulating tool 10 shown in FIG. 1 includes a body 12 and a nut 14 threaded onto an end of the body. The body 12 may be considered as having a proximal end (to the left in FIG. 1) and a distal end (to the right in FIG. 1). The body 12 includes a cylindrical portion 13 at its proximal end and an integral collet portion 16 at its distal end. The collet 16 is tapered distally and includes four circumferentially spaced arms 18 separated by radial, longitudinally extending slots 30. A reduced diameter 20 neck extends between the collet 16 and the cylindrical portion 13.

The body 12 includes a longitudinally extending bore 22 that narrows at tapered portion 24 from a wider diameter at the proximal end to a narrower diameter diameter 26 at its distal portion. The bore 22 passes through the collet 16 and is open at the distal end defining an exit opening 26. The bore 22 also is exposed laterally through a radial, longitudinally extending slot 31 formed in the body 12. The slot 31 is sized to permit passage of a guidewire. In the preferred embodiment, the slot has a width of at least 0.020 inches in order to accommodate commercially available coronary guidewires that range typically between 0.010 and 0.018 inches. Preferably, one of the slots 30 in the collet 16 is a continuation of the lateral slot 31 and may be wider than the other slots 30 in the collet.

The collet 16 includes a substantially constant diameter threaded portion 32 and a distally tapering, generally conical portion 34 The front edges 38 of the collet arms 18 are bevelled to provide collectively a concave surface for facilitating mounting of the tool 10 to the guidewire in the traditional longitudinal fashion. The nut 14 includes an internal conical surface that is drawn against and closes the collet arms 18 when the nut 14 is tightened about the collet 16. The nut 14 includes a lateral, longitudinally extending slot 44 that is alignable with the slot 31 in the tool 10. The slot 44 also is sized to receive a guidewire and, preferably, has a width of at least 0.020 inches. The surface of the main body 12 and the nut 14 may be knurled 46 to enhance the users grip on the device.

The main body 12 and the nut 40 preferably are formed of brass or other metal such as aluminum, stainless steel or alloys of brass, aluminum or stainless steel. Hard plastics such as polyvinylchloride, acrylics, polycarbonate or polystyrene also are contemplated. In one alternative embodiment, the device includes a plastic body and a metal collet bonded with an adhesive to the distal end thereof. The collet or the outer surface of the distal end may be threaded for engagement with the metal nut. In a preferred embodiment, the tool is 2 inches long and has an outside diameter of between 0.250 inches and 0.3125 inches. The diameter of the longitudinally extending bore ranges from 0.020 inches to 0.030 inches.

Figure 2:
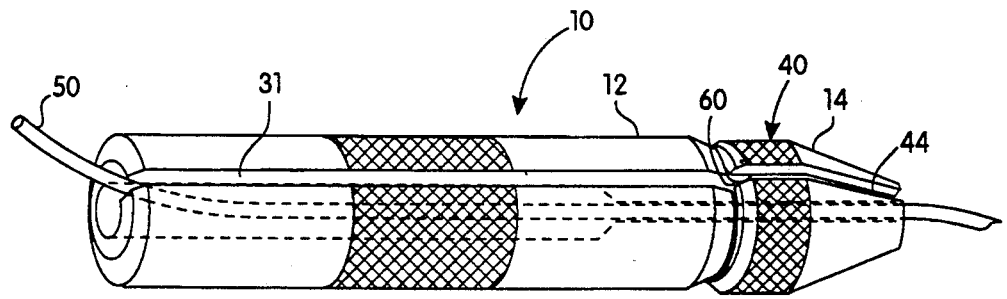
FIG. 2 is a perspective view, partly in phantom, of the guidewire manipulating tool being laterally mounted to the guidewire.
Figure 3:
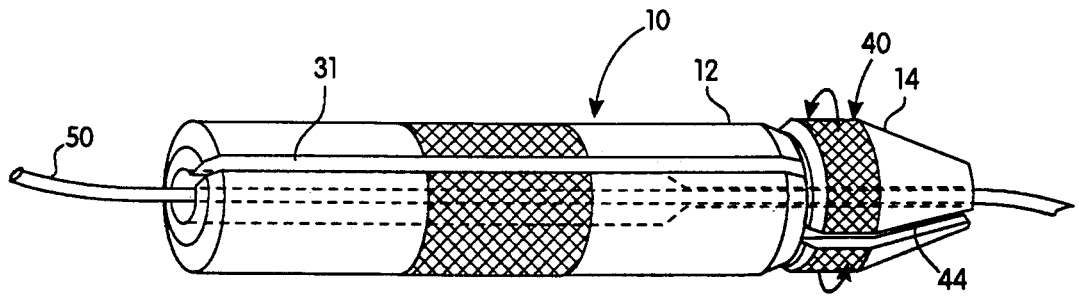
FIG. 3 is a perspective view, partly in phantom, of the guidewire manipulating tool in accordance with the invention with the guidewire fixedly positioned within the tool.
Figure 4:
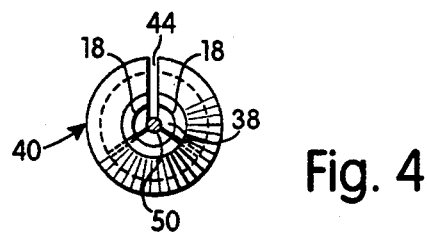
FIG. 4 is an end view of the guidewire manipulating tool in accordance with the invention showing the guidewire fixedly positioned between the collet arms.

The lateral mounting of the tool 10 on a guidewire 50 is shown in FIGS. 2-3. The nut 14 loosely is threaded on the collet 16 with the slot 44 in the nut 14 aligned with the slot 31 in the body 12, thus defining a continuously open slot receptive to the guidewire 50. The tool 10 then is laterally mounted onto the guidewire 50 and the nut 14 is tightened to cause the collet arms 18 to grip the guidewire 50 as shown in FIG. 4. Once the nut 40 is sufficiently tightened, the guidewire may be steered or otherwise manipulated by movement of the tool 10 to which it is securely attached. The tool 10 is removed easily from the guidewire by loosening the nut 40 to release the grip of the collet arms 18. The slot 44 in the nut 14 then is aligned with the slot 31 in the body 12 to permit lateral detachment of the tool from the guidewire 50.

The tool 10 also may be mounted on the guidewire 50 in the traditional longitudinal manner by threading the device onto an end of the guidewire. With the nut 14 loosely threaded onto the collet 16, the tool 10 may be threaded onto the proximal or the distal end of the guidewire 50 and slid along the guidewire to a location convenient for the physician. After the tool has been advanced to the desired location on the guidewire 50, the nut 14 is tightened to lock the tool to the guidewire.

It should be understood that the foregoing description of the invention is intended merely to be illustrative thereof and that other equivalents, embodiments and modifications of the invention may be apparent to those skilled in the art.

What is claimed is:

1. A tool for manipulating a guidewire, comprising:
   an elongated body having a bore extending therethrough and a longitudinal slot extending radially from said bore through the surface of said elongated body, said slot and said bore being adapted to receive the guidewire;
   one end of said elongated body including a collet portion, said collet portion having a plurality of radial, longitudinally extending slots extending from said elongated bore through the surface of said collet portion, a portion of said surface of said collet portion being threaded; and
   a nut threadably mounted to said collet portion and having a bore extending therethrough, said nut having a radial, longitudinally extending slot extending radially from said nut bore through the surface of said nut, said radial, longitudinally extending slot in said nut being registerable with said radial, longitudinally extending slot in said elongated body to form a continuous elongated slot along the length of said tool, said continuous elongated slot being adapted to receive the guidewire.

2. The tool recited in claim 1 wherein each of said plurality of radial, longitudinally extending slots in said collet portion is narrower than said radial, longitudinally extending slot in said body.

3. The tool recited in claim 1 wherein one of said plurality of radial, longitudinally extending slots in said collet portion includes said radial, longitudinally extending slot in said body.

4. The tool recited in claim 3 wherein said one of said plurality of radial, longitudinally extending slots in said collet portion is wider than the other of said plurality of radial, longitudinally extending slots in said collet portion.

5. The tool recited in claim 3 wherein said one of said plurality of radial, longitudinally extending slots in said collet portion is a continuation of said radial, longitudinally extending slot in said body.

6. The tool recited in claim 1 wherein said radial, longitudinally extending slot in said body has a width of at least 0.020 inches.

7. The tool recited in claim 6 wherein one of said plurality of radial, longitudinally extending slots in said collet portion has a width of at least 0.020 inches.

8. The tool recited in claim 7 wherein said radial, longitudinally extending slot in said nut has a width of at least 0.020 inches.

9. The tool recited in claim 1 wherein said radial, longitudinally extending slot in said body and said radial, longitudinally extending slot in said nut have the same width.

10. The tool recited in claim 1 wherein said continuous elongated slot has a uniform width.

11. A tool for manipulating a guidewire comprising:
    an elongated body having a bore extending axially therethrough, said elongated body having an opening laterally extending from said elongated bore through the surface of said elongated body, said laterally extending opening in said body being adapted to receive the guidewire;
    said elongated body including a collet portion having a plurality of spaced slots radially extending from said elongated bore through the surface of said collet portion, one of said plurality of spaced radially extending slots including said laterally extending opening extending through said collet portion and having a width larger than the width of the other of said plurality of spaced radially extending slots, a portion of said surface of said collet portion being threaded; and a nut threadably mounted to said collet portion and having a bore extending axially therethrough, said nut having a slot laterally extending from said bore through the surface of said nut, said laterally extending slot in said nut being alignable with said laterally extending opening in said elongated body to form a continuous elongated slot along the length of said tool, said continuous elongated slot being adapted to receive the guidewire.

* * * * *